United States Patent
Baileykobayashi et al.

(10) Patent No.: US 11,505,589 B2
(45) Date of Patent: Nov. 22, 2022

(54) ANTITUMOR PEPTIDE AND USE THEREOF

(71) Applicants: TOAGOSEI CO., LTD., Tokyo (JP); National University Corporation Nagoya University, Aichi-ken (JP)

(72) Inventors: Nahoko Baileykobayashi, Tsukuba-Ibaraki-ken (JP); Tetsuhiko Yoshida, Tsukuba (JP); Makoto Sawada, Nagoya (JP)

(73) Assignees: TOAGOSEI CO., LTD, Tokyo (JP); National University Corporation Nagoya University, Aichi-ken (JP)

(*) Notice: Subject to any disclaimer, the term of this patent is extended or adjusted under 35 U.S.C. 154(b) by 53 days.

(21) Appl. No.: 16/665,101

(22) Filed: Oct. 28, 2019

(65) Prior Publication Data
US 2020/0148740 A1    May 14, 2020

(30) Foreign Application Priority Data

Nov. 8, 2018  (JP) .............. JP2018-210913
Jul. 24, 2019  (JP) .............. JP2019-135840

(51) Int. Cl.
  *C07K 14/705* (2006.01)
  *C07K 14/47* (2006.01)
  *A61P 35/00* (2006.01)
  *A61K 38/00* (2006.01)

(52) U.S. Cl.
  CPC ........ *C07K 14/70503* (2013.01); *A61P 35/00* (2018.01); *C07K 14/47* (2013.01); *A61K 38/00* (2013.01); *C07K 2319/03* (2013.01); *C07K 2319/33* (2013.01)

(58) Field of Classification Search
None
See application file for complete search history.

(56) References Cited

U.S. PATENT DOCUMENTS 8,703,915 B2 * 4/2014 Jazayeri-Dezfuly ........................ C07K 14/705
530/350

OTHER PUBLICATIONS

Sukocheva, Olga A. "Expansion of Sphingosine Kinase and Sphingosine-1-Phosphate Receptor Function in Normal and Cancer Cells: From Membrane Restructuring to Mediation of Estrogen Signaling and Stem Cell Programming." International Journal of Molecular Sciences, 19, 420 (Jan. 2018) p. 1-31.
Pyne et al. "Sphingosine 1-Phosphate and Cancer." Nature Reviews, vol. 10 (Jul. 2010) p. 489-503.

* cited by examiner

Primary Examiner — Julie Ha
Assistant Examiner — Tara L Martinez
(74) Attorney, Agent, or Firm — Occhiuti & Rohlicek LLP

(57) ABSTRACT

An antitumor peptide provided according to the present invention includes
(1) an S1PR-TM related sequence; and
(2) an amino acid sequence functioning as a cell penetrating peptide;
wherein the total number of amino acid residues is 100 or less.

2 Claims, No Drawings
Specification includes a Sequence Listing.

SEQUENCE LISTING

<160> NUMBER OF SEQ ID NOS: 41

<210> SEQ ID NO 1
<211> LENGTH: 29

```
<212> TYPE: PRT
<213> ORGANISM: Artificial Sequence
<220> FEATURE:
<223> OTHER INFORMATION: synthetic peptide

<400> SEQUENCE: 1

Ala Met Tyr Leu Phe Leu Gly Asn Leu Ala Ala Ser Asp Leu Leu Ala
1               5                   10                  15
Gly Val Ala Phe Val Ala Asn Thr Leu Leu Ser Gly Ser
            20                  25

<210> SEQ ID NO 2
<211> LENGTH: 21
<212> TYPE: PRT
<213> ORGANISM: Artificial Sequence
<220> FEATURE:
<223> OTHER INFORMATION: synthetic peptide

<400> SEQUENCE: 2

Leu Val Asn Ile Thr Leu Ser Asp Leu Leu Thr Gly Ala Ala Tyr Leu
1               5                   10                  15
Ala Asn Val Leu Leu
            20

<210> SEQ ID NO 3
<211> LENGTH: 21
<212> TYPE: PRT
<213> ORGANISM: Artificial Sequence
<220> FEATURE:
<223> OTHER INFORMATION: synthetic peptide

<400> SEQUENCE: 3

Trp Phe Leu Arg Glu Gly Leu Leu Phe Thr Ala Leu Ala Ala Ser Thr
1               5                   10                  15
Phe Ser Leu Leu Phe
            20

<210> SEQ ID NO 4
<211> LENGTH: 21
<212> TYPE: PRT
<213> ORGANISM: Artificial Sequence
<220> FEATURE:
<223> OTHER INFORMATION: synthetic peptide

<400> SEQUENCE: 4

Val Tyr Gly Phe Ile Gly Leu Cys Trp Leu Leu Ala Ala Leu Leu Gly
1               5                   10                  15
Met Leu Pro Leu Leu
            20

<210> SEQ ID NO 5
<211> LENGTH: 21
<212> TYPE: PRT
<213> ORGANISM: Artificial Sequence
<220> FEATURE:
<223> OTHER INFORMATION: synthetic peptide

<400> SEQUENCE: 5

Glu Gly Gly Val Phe Val Ala Leu Thr Ala Ser Val Leu Ser Leu Leu
1               5                   10                  15
Ala Ile Ala Leu Glu
            20

<210> SEQ ID NO 6
```

```
<211> LENGTH: 21
<212> TYPE: PRT
<213> ORGANISM: Artificial Sequence
<220> FEATURE:
<223> OTHER INFORMATION: synthetic peptide

<400> SEQUENCE: 6

Leu Ala Met Ala Ala Ala Ala Trp Gly Val Ser Leu Leu Leu Gly Leu
1               5                   10                  15

Leu Pro Ala Leu Gly
            20

<210> SEQ ID NO 7
<211> LENGTH: 29
<212> TYPE: PRT
<213> ORGANISM: Artificial Sequence
<220> FEATURE:
<223> OTHER INFORMATION: synthetic peptide

<400> SEQUENCE: 7

Ala Met Tyr Leu Phe Leu Gly Asn Leu Ala Ala Ser Asp Leu Leu Ala
1               5                   10                  15

Gly Val Ala Phe Val Ala Asn Thr Leu Leu Ser Gly His
            20                  25

<210> SEQ ID NO 8
<211> LENGTH: 29
<212> TYPE: PRT
<213> ORGANISM: Artificial Sequence
<220> FEATURE:
<223> OTHER INFORMATION: synthetic peptide

<400> SEQUENCE: 8

Ala Met Tyr Leu Phe Leu Gly Asn Leu Ala Ala Ser Asp Leu Leu Ala
1               5                   10                  15

Gly Val Ala Phe Val Ala Asn Thr Leu Leu Ser Gly Pro
            20                  25

<210> SEQ ID NO 9
<211> LENGTH: 21
<212> TYPE: PRT
<213> ORGANISM: Artificial Sequence
<220> FEATURE:
<223> OTHER INFORMATION: synthetic peptide.

<400> SEQUENCE: 9

Leu Leu Asn Ile Thr Leu Ser Asp Leu Leu Thr Gly Leu Ala Tyr Val
1               5                   10                  15

Val Asn Val Leu Leu
            20

<210> SEQ ID NO 10
<211> LENGTH: 21
<212> TYPE: PRT
<213> ORGANISM: Artificial Sequence
<220> FEATURE:
<223> OTHER INFORMATION: synthetic peptide

<400> SEQUENCE: 10

Trp Phe Leu Arg Glu Gly Leu Leu Phe Met Ala Leu Ala Ala Ser Thr
1               5                   10                  15

Phe Ser Leu Leu Phe
            20
```

```
<210> SEQ ID NO 11
<211> LENGTH: 21
<212> TYPE: PRT
<213> ORGANISM: Artificial Sequence
<220> FEATURE:
<223> OTHER INFORMATION: synthetic peptide

<400> SEQUENCE: 11

Val Tyr Gly Phe Ile Gly Leu Cys Trp Leu Leu Ala Ala Leu Leu Gly
1               5                   10                  15

Met Leu Pro Leu Leu
            20

<210> SEQ ID NO 12
<211> LENGTH: 23
<212> TYPE: PRT
<213> ORGANISM: Artificial Sequence
<220> FEATURE:
<223> OTHER INFORMATION: synthetic peptide

<400> SEQUENCE: 12

Val Tyr Gly Phe Ile Gly Leu Cys Trp Leu Leu Ala Gly Leu Leu Gly
1               5                   10                  15

Leu Leu Pro Leu Leu Gly Trp
            20

<210> SEQ ID NO 13
<211> LENGTH: 23
<212> TYPE: PRT
<213> ORGANISM: Artificial Sequence
<220> FEATURE:
<223> OTHER INFORMATION: synthetic peptide

<400> SEQUENCE: 13

Val Cys Ser Phe Ile Gly Leu Cys Trp Leu Leu Ala Thr Leu Leu Gly
1               5                   10                  15

Leu Leu Pro Leu Leu Gly Trp
            20

<210> SEQ ID NO 14
<211> LENGTH: 21
<212> TYPE: PRT
<213> ORGANISM: Artificial Sequence
<220> FEATURE:
<223> OTHER INFORMATION: synthetic peptide

<400> SEQUENCE: 14

Glu Gly Gly Val Phe Val Ala Leu Ala Ala Ser Val Leu Ser Leu Leu
1               5                   10                  15

Ala Ile Ala Leu Glu
            20

<210> SEQ ID NO 15
<211> LENGTH: 21
<212> TYPE: PRT
<213> ORGANISM: Artificial Sequence
<220> FEATURE:
<223> OTHER INFORMATION: synthetic peptide

<400> SEQUENCE: 15

Leu Ala Met Ala Val Ala Ala Trp Gly Ala Ser Leu Leu Leu Gly Leu
1               5                   10                  15

Leu Pro Ala Leu Gly
            20
```

<210> SEQ ID NO 16
<211> LENGTH: 21
<212> TYPE: PRT
<213> ORGANISM: Artificial Sequence
<220> FEATURE:
<223> OTHER INFORMATION: synthetic peptide

<400> SEQUENCE: 16

Leu Ala Met Ala Val Ala Ala Trp Gly Leu Ser Leu Leu Gly Leu
1               5                   10                  15

Leu Pro Ala Leu Gly
            20

<210> SEQ ID NO 17
<211> LENGTH: 21
<212> TYPE: PRT
<213> ORGANISM: Artificial Sequence
<220> FEATURE:
<223> OTHER INFORMATION: synthetic peptide

<400> SEQUENCE: 17

Leu Ala Leu Ala Ala Gly Ala Trp Gly Val Ser Leu Leu Gly Leu
1               5                   10                  15

Leu Pro Ala Leu Gly
            20

<210> SEQ ID NO 18
<211> LENGTH: 14
<212> TYPE: PRT
<213> ORGANISM: Artificial Sequence
<220> FEATURE:
<223> OTHER INFORMATION: synthetic peptide

<400> SEQUENCE: 18

Arg Ser Arg Lys Tyr Thr Ser Trp Tyr Val Ala Leu Lys Arg
1               5                   10

<210> SEQ ID NO 19
<211> LENGTH: 19
<212> TYPE: PRT
<213> ORGANISM: Artificial Sequence
<220> FEATURE:
<223> OTHER INFORMATION: synthetic peptide

<400> SEQUENCE: 19

Met Ala Lys Ser Ile Arg Ser Lys His Arg Arg Gln Met Arg Met Met
1               5                   10                  15

Lys Arg Glu

<210> SEQ ID NO 20
<211> LENGTH: 16
<212> TYPE: PRT
<213> ORGANISM: Artificial Sequence
<220> FEATURE:
<223> OTHER INFORMATION: synthetic peptide

<400> SEQUENCE: 20

Met Ala Arg Arg Arg Arg His Arg Gly Pro Arg Arg Pro Arg Pro Pro
1               5                   10                  15

<210> SEQ ID NO 21
<211> LENGTH: 19
<212> TYPE: PRT
<213> ORGANISM: Artificial Sequence
<220> FEATURE:

```
<223> OTHER INFORMATION: synthetic peptide

<400> SEQUENCE: 21

Gly Arg Cys Arg Arg Leu Ala Asn Phe Gly Pro Arg Lys Arg Arg Arg
1               5                   10                  15

Arg Arg Arg

<210> SEQ ID NO 22
<211> LENGTH: 16
<212> TYPE: PRT
<213> ORGANISM: Artificial Sequence
<220> FEATURE:
<223> OTHER INFORMATION: synthetic peptide

<400> SEQUENCE: 22

Arg Arg Arg Lys Arg Asn Arg Asp Ala Arg Arg Arg Arg Lys Gln
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: synthetic peptide

<400> SEQUENCE: 23

Met Gln Arg Lys Pro Thr Ile Arg Arg Lys Asn Leu Arg Leu Arg Arg
1               5                   10                  15

Lys

<210> SEQ ID NO 24
<211> LENGTH: 7
<212> TYPE: PRT
<213> ORGANISM: Artificial Sequence
<220> FEATURE:
<223> OTHER INFORMATION: synthetic peputide

<400> SEQUENCE: 24

Ile Met Arg Arg Arg Gly Leu
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic peptide

<400> SEQUENCE: 25

Lys Lys Leu Lys Lys Arg Asn Lys
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic peptide

<400> SEQUENCE: 26

Arg Arg Arg Ala Asn Asn Arg Arg Arg
1               5

<210> SEQ ID NO 27
<211> LENGTH: 7
```

```
<212> TYPE: PRT
<213> ORGANISM: Artificial Sequence
<220> FEATURE:
<223> OTHER INFORMATION: synthetic peptide

<400> SEQUENCE: 27

Arg Lys Lys Arg Lys Lys Lys
1               5

<210> SEQ ID NO 28
<211> LENGTH: 15
<212> TYPE: PRT
<213> ORGANISM: Artificial Sequence
<220> FEATURE:
<223> OTHER INFORMATION: synthetic peptide

<400> SEQUENCE: 28

Lys Arg Lys Gly Lys Leu Lys Asn Lys Gly Ser Lys Arg Lys Lys
1               5                   10                  15

<210> SEQ ID NO 29
<211> LENGTH: 18
<212> TYPE: PRT
<213> ORGANISM: Artificial Sequence
<220> FEATURE:
<223> OTHER INFORMATION: synthetic peptide

<400> SEQUENCE: 29

Ser Lys Arg Leu Ser Ser Arg Ala Arg Lys Arg Ala Ala Lys Arg Arg
1               5                   10                  15

Leu Gly

<210> SEQ ID NO 30
<211> LENGTH: 14
<212> TYPE: PRT
<213> ORGANISM: Artificial Sequence
<220> FEATURE:
<223> OTHER INFORMATION: synthetic peptide

<400> SEQUENCE: 30

Lys Arg Pro Arg Arg Arg Pro Ser Arg Pro Phe Arg Lys Pro
1               5                   10

<210> SEQ ID NO 31
<211> LENGTH: 13
<212> TYPE: PRT
<213> ORGANISM: Artificial Sequence
<220> FEATURE:
<223> OTHER INFORMATION: synthetic peptide

<400> SEQUENCE: 31

Lys Lys Arg Thr Leu Arg Lys Asn Asp Arg Lys Lys Arg
1               5                   10

<210> SEQ ID NO 32
<211> LENGTH: 8
<212> TYPE: PRT
<213> ORGANISM: Artificial Sequence
<220> FEATURE:
<223> OTHER INFORMATION: synthetic peputide

<400> SEQUENCE: 32

Trp Arg Arg Gln Ala Arg Phe Lys
1               5

<210> SEQ ID NO 33
```

```
<211> LENGTH: 9
<212> TYPE: PRT
<213> ORGANISM: Artificial Sequence
<220> FEATURE:
<223> OTHER INFORMATION: synthetic peptide

<400> SEQUENCE: 33

Arg Lys Lys Arg Arg Gln Arg Arg Arg
1               5

<210> SEQ ID NO 34
<211> LENGTH: 11
<212> TYPE: PRT
<213> ORGANISM: Artificial Sequence
<220> FEATURE:
<223> OTHER INFORMATION: synthetic peptide

<400> SEQUENCE: 34

Tyr Ala Arg Ala Ala Ala Arg Gln Ala Arg Ala
1               5                   10

<210> SEQ ID NO 35
<211> LENGTH: 18
<212> TYPE: PRT
<213> ORGANISM: Artificial Sequence
<220> FEATURE:
<223> OTHER INFORMATION: synthetic peptide

<400> SEQUENCE: 35

Lys Gly Arg Gln Val Lys Val Trp Phe Gln Asn Arg Arg Met Lys Trp
1               5                   10                  15

Lys Lys

<210> SEQ ID NO 36
<211> LENGTH: 38
<212> TYPE: PRT
<213> ORGANISM: Artificial Sequence
<220> FEATURE:
<223> OTHER INFORMATION: synthetic peptide

<400> SEQUENCE: 36

Ala Met Tyr Leu Phe Leu Gly Asn Leu Ala Ala Ser Asp Leu Leu Ala
1               5                   10                  15

Gly Val Ala Phe Val Ala Asn Thr Leu Leu Ser Gly Ser Arg Lys Lys
            20                  25                  30

Arg Arg Gln Arg Arg Arg
        35

<210> SEQ ID NO 37
<211> LENGTH: 30
<212> TYPE: PRT
<213> ORGANISM: Artificial Sequence
<220> FEATURE:
<223> OTHER INFORMATION: synthetic peptide

<400> SEQUENCE: 37

Leu Val Asn Ile Thr Leu Ser Asp Leu Leu Thr Gly Ala Ala Tyr Leu
1               5                   10                  15

Ala Asn Val Leu Leu Arg Lys Lys Arg Arg Gln Arg Arg Arg
            20                  25                  30

<210> SEQ ID NO 38
<211> LENGTH: 30
<212> TYPE: PRT
<213> ORGANISM: Artificial Sequence
```

```
<220> FEATURE:
<223> OTHER INFORMATION: synthetic peptide

<400> SEQUENCE: 38

Trp Phe Leu Arg Glu Gly Leu Leu Phe Thr Ala Leu Ala Ala Ser Thr
1               5                   10                  15

Phe Ser Leu Leu Phe Arg Lys Lys Arg Arg Gln Arg Arg
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: synthetic peptide

<400> SEQUENCE: 39

Val Tyr Gly Phe Ile Gly Leu Cys Trp Leu Leu Ala Ala Leu Leu Gly
1               5                   10                  15

Met Leu Pro Leu Leu Arg Lys Lys Arg Arg Gln Arg Arg
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: synthetic peptide

<400> SEQUENCE: 40

Glu Gly Gly Val Phe Val Ala Leu Thr Ala Ser Val Leu Ser Leu Leu
1               5                   10                  15

Ala Ile Ala Leu Glu Arg Lys Lys Arg Arg Gln Arg Arg
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: synthetic peptide

<400> SEQUENCE: 41

Leu Ala Met Ala Ala Ala Ala Trp Gly Val Ser Leu Leu Leu Gly Leu
1               5                   10                  15

Leu Pro Ala Leu Gly Arg Lys Lys Arg Arg Gln Arg Arg
            20                  25                  30
```

ANTITUMOR PEPTIDE AND USE THEREOF

CROSS-REFERENCE TO RELATED APPLICATIONS

Priority is claimed on Japanese Patent Application No. 2018-210913, filed Nov. 8, 2018, and Japanese Patent Application No. 2019-135840, filed on Jul. 24, 2019, the content of which is incorporated herein by reference.

In addition, on Oct. 30, 2018, Nahoko Bailey Kobayashi, Makoto Sawada, Yoshinori Hasegawa, and Tetsuhiko Yoshida disclosed "A peptide based on transmembrane domain of S1PR1 as a tumor cell growth inhibitor" in the session of Searchable Programme "PB-039", 30th EORTC-NCI-AACR SYMPOSIUM published on the website at the following address. https://www.ecco-org.eu/Events/ENA2018/Searchable-Programme#anchorScpr The publishers Nahoko Bailey Kobayashi, Tetsuhiko Yoshida, and Makoto Sawada are the inventors of this disclosure. In addition, the publisher Yoshinori Hasegawa is listed among the publishers only as an advisor for experimental processes. This application is subject to the provisions of 35 U.S.C. 102(b)(1) for the above publication.

TECHNICAL FIELD

The present invention relates to an artificially synthesized antitumor peptide that can inhibit proliferation of tumor cells and use thereof, and specifically, to use of an artificial peptide including an amino acid sequence constituting a transmembrane (TM) region of proteins belonging to the sphingosine 1-phosphate receptor (S1PR) family (hereinafter referred to as a "TM sequence") and a cell-penetrating peptide sequence.

TECHNICAL BACKGROUND

Many studies in which sphingosine 1-phosphate (S1P), which is one of components constituting a cell membrane, promoted cancer progression have been reported in recent years. It has been reported that S1P levels in the serum of cancer patients were higher than those in healthy people, and cancer patients had increased expression of SP synthase sphingosine kinase 1 (SphK1) and the receptor S1PR. Non-patent literature by Sukocheva (Olga A. Sukocheva, International Journal of Molecular Sciences, 2018, 19, 420) and another non-patent literature by Pyne et al. (Nigel J. Pyne and Susan Pyne, Nature Reviews, 2010, 10, 489-503) can be referred to. It has been reported that, in vitro, S1P promotes tumor cell proliferation and metastasis, and promotes inflammation and angiogenesis in the tumor microenvironment, and thereby conditions suitable for tumor growth are provided. Therefore, SphK1 and S1PR can be treatment targets in novel cancer treatments, and studies regarding these have been actively conducted.

Incidentally, nowadays, studies regarding treatments targeting disease-specific molecules are rapidly progressing, and many molecularly targeted drugs including antibody drugs have been developed. Regarding an example of molecular targeting treatments for cancer, in recent years, molecular targeted drugs targeting MAPK signaling pathway-related molecules (BRAF etc.) have been developed, and applied to, for example, a melanoma treatment. The molecular targeted drugs temporarily exhibit particularly excellent antitumor effects on target cancers, but drug-resistant cancer cells may appear after a certain time. In addition, antitumor agents in which antibodies are used as pharmacologically effective components are very expensive and lead to serious situations in which a problem of high cancer treatment cost is not avoidable.

SUMMARY OF THE INVENTION

Thus, an object (purpose) of the present invention is to provide a synthetic peptide having a structure and antitumor (anti-cancer) mechanism different from those of antitumor agents in which expensive antibodies are used.

The inventors have focused on the TM region of proteins belonging to the seven transmembrane protein S1PR family expressed in various species, and particularly, mammals. Thus, they surprisingly found that a synthetic peptide in which, particularly, amino acid sequences constituting the TM region of S1PR2, S1PR4, and S1PR5 and amino acid sequences constituting a conventionally known cell penetrating peptide (CPP) are combined has excellent antitumor properties (anti-cancer properties) with respect to various tumor cells, and thereby the present invention was completed.

Specifically, the synthetic peptide disclosed here is a synthetic peptide inhibiting proliferation of at least one type of tumor cells, and comprising both amino acid sequences indicated in following (1) and (2):
(1) an S1PR-TM related sequence, an amino acid sequence constituting a transmembrane (TM) region of a membrane protein sphingosine 1-phosphate receptor (S1PR) and represented by any one of the following i) to vi):
i) an amino acid sequence constituting the 2nd TM region from the N-terminal of S1PR2; or a modified amino acid sequence formed by deletion, substitution or addition of 1, 2, or 3 amino acid residues in the amino acid sequence;
ii) an amino acid sequence constituting the 2nd TM region from the N-terminal of S1PR4; or a modified amino acid sequence formed by deletion, substitution or addition of 1, 2, or 3 amino acid residues in the amino acid sequence;
iii) an amino acid sequence constituting the 3rd TM region from the N-terminal of S1PR4; or a modified amino acid sequence formed by deletion, substitution or addition of 1, 2, or 3 amino acid residues in the amino acid sequence;
iv) an amino acid sequence constituting the 4th TM region from the N-terminal of S1PR4; or a modified amino acid sequence formed by deletion, substitution or addition of 1, 2, or 3 amino acid residues in the amino acid sequence;
v) an amino acid sequence constituting the 3rd TM region from the N-terminal of S1PR5; or a modified amino acid sequence formed by deletion, substitution or addition of 1, 2, or 3 amino acid residues in the amino acid sequence;
vi) an amino acid sequence constituting the 4th TM region from the N-terminal of S1PR5; or a modified amino acid sequence formed by deletion, substitution or addition of 1, 2, or 3 amino acid residues in the amino acid sequence; and
(2) an amino acid sequence functioning as a cell-penetrating peptide (CPP) (hereinafter referred to as a "CPP related sequence").

In a preferable aspect, the total number of amino acid residues in the antitumor peptide disclosed here is 100 or less. In consideration of production costs, ease of synthesis, and handling properties, the total number of amino acid residues is more preferably 80 or less (for example, 70 or less).

Alternatively, a synthetic peptide in which a proportion of the amino acid sequences indicated in (1) and the amino acid sequences indicated in (2) is 80% or more by number (more preferably 90% or more by number, for example, 100% or more by number) in the whole amino acid sequence is a particularly preferable aspect in the antitumor peptide disclosed here.

An amino acid sequence represented by any one of SEQ ID NOs: 1 to 17 is typical example of the S1PR-TM related sequence that can be suitably used for implementation of the present invention.

In addition, in another preferable aspect of the antitumor peptide disclosed here, the CPP related sequence is a polyarginine (although not particularly limited, typically, composed of 5 or more and 9 or less arginine residues), or an amino acid sequence represented by any one of SEQ ID NOs: 18 to 35, or a modified amino acid sequence having one, two, or three amino acid deletion, substitution or addition in the amino acid sequence.

For example, a synthetic peptide including both
(i) an amino acid sequence represented by any one of SEQ ID NOs: 1 to 6 or a modified amino acid sequence formed by deletion, substitution or addition of 1 or more (for example, 2 or 3) amino acid residues in the amino acid sequences; and
(ii) a polyarginine or an amino acid sequence represented by any one of SEQ ID NOs: 18 to 35, or a modified amino acid sequence formed by deletion, substitution or addition of 1 or more (for example, 2 or 3) amino acid residues in the amino acid sequences, may be exemplified as a preferable example.

In another preferable aspect of the antitumor peptide disclosed here, the CPP related sequence (or its modified amino acid sequence) is adjacent to the N-terminal or C-terminal side of the S1PR-TM related sequence. Alternatively, the CPP related sequence is arranged via 10 or less (preferably 5 or less, for example, 1 or 2) amino acid residues functioning as a linker.

In a preferable aspect, the antitumor peptide disclosed here comprises an amino acid sequence represented by any one of SEQ ID NOs: 36 to 41.

In addition, the present invention provides an antitumor composition comprising any one of the synthetic peptides (antitumor peptides) disclosed here and at least one pharmaceutically acceptable carrier, and inhibiting proliferation of at least one type of tumor cells.

Such a composition comprising an antitumor peptide disclosed here can be used as an antitumor agent (including an anti-cancer agent; hereinafter the same) or a material for development of a novel antitumor agent.

In addition, the present invention provides a method for inhibiting proliferation of at least one type of tumor cells comprising supplying of any one of the synthetic peptides (antitumor peptides) disclosed here to target tumor cells (for example, outside a living organism=in vitro, or inside a living organism=in vivo) at least once.

In the method in such a configuration, when the antitumor peptide disclosed here is supplied to tumor cells, it is possible to prevent or inhibit proliferation (and hence, enlargement in tumor and cancer tissues) of the tumor cells.

DESCRIPTION OF THE RELATED EMBODIMENTS

Preferable embodiments of the present invention will be described below. Components other than those particularly mentioned in this specification (for example, the primary structure and chain length of the synthetic peptide disclosed here) that are necessary for implementation of the present invention (for example, a method of chemically synthesizing a peptide, a cell culture technique, and a general method of preparing a pharmaceutical composition including a peptide as a component) can be recognized by those skilled in the art as design matters based on the related art in the fields of cell engineering, physiology, medicine, pharmacy, organic chemistry, biochemistry, genetic engineering, protein engineering, molecular biology, genetics, and the like. The present invention can be implemented based on content disclosed in this specification and common general technical knowledge in the field. Here, in the following description, amino acids are represented by one-letter symbols (but, three-letter symbols in the sequence listing).

The entire content of all documents cited in this specification is incorporated herein by reference.

In this specification, "tumor" is a term that is interpreted in a broad sense, and refers to a general tumor (typically, a malignant tumor) including a carcinoma and sarcoma or blood or hematopoietic tissue lesions (leukemia, lymphoma, etc.). In addition, "tumor cell" is the same as "cancer cell," and refers to cells that form such a tumor and cells (so-called cancerous cells) that typically abnormally proliferate regardless of surrounding normal tissues. Therefore, unless otherwise specified, cells that are classified as tumor cells (cancer cells) rather than normal cells are referred to as tumor cells regardless of the origin or properties of the cells. Cells constituting epithelial tumors (squamous cell carcinoma, adenocarcinoma, etc.), non-epithelial tumors (various sarcomas and osteosarcomas, etc.), various cell tumors (neuroblastoma, retinoblastoma, etc.), lymphoma, melanoma, or the like are typical examples included in the tumor cells mentioned here.

In addition, "synthetic peptide" in this specification refers to a peptide fragment of which a peptide chain alone is not independently and stably present in nature, but is produced through artificial chemical synthesis or biosynthesis (that is, production based on genetic engineering) and can be stably present in a predetermined composition. Here, the term "peptide" refers to an amino acid polymer having a plurality of peptide bonds, and although the number of amino acid residues included in the peptide chain is not limited, the peptide is a relatively low molecular-weight polymer, typically, a total number of amino acid residues being about 100 or less (preferably 80 or less, more preferably 70 or less, and particularly preferably 50 or less).

In addition, the term "amino acid residue" in this specification includes an N-terminal amino acid and a C-terminal amino acid of a peptide chain unless otherwise specified.

Here, always, the left side of the amino acid sequences described in this specification is the N-terminal side, and the right side thereof is the C-terminal side.

The "modified amino acid sequence" with respect to a predetermined amino acid sequence in this specification refers to an amino acid sequence formed when one to several (typically, 9 or less, and preferably 5 or less) amino acid residues, for example, one, two, or three amino acid residues, are substituted, deleted or added (inserted) without impairing functions (for example, antitumor activity and cell membrane penetrating ability) of the predetermined amino acid sequence. For example, a sequence generated by so-called conservative substitution (conservative amino acid replacement) in which one, two, or three amino acid residues are conservatively substituted (for example, a sequence in which a basic amino acid residue is substituted with another basic amino acid residue; for example, a lysine residue and an arginine residue are substituted with each other), a sequence having one, two, or three amino acid addition (insertion) or deletion in a predetermined amino acid sequence, and the like are typical examples included in the modified amino acid sequence referred to in this specification. Accordingly, the antitumor peptide disclosed as an example here includes, in addition to a synthetic peptide composed of the same amino acid sequence as the amino acid sequence represented by each of the SEQ ID NOs, synthetic peptides composed of modified amino acid sequences having one, two, or three amino acid substitution (for example, the above conservative substitution), deletion or addition in the amino acid sequences represented by respective SEQ ID NOs and exhibiting the same antitumor activity.

The artificially synthesized antitumor peptide disclosed here is a short chain peptide that does not occur in nature and that the inventors found to inhibit tumor cell proliferation (that is, antitumor activity), and is a peptide including the above two amino acid sequences, that is, (1) an S1PR-TM related sequence, and
(2) a CPP related sequence.

Here, the S1PR-TM related sequence refers to an amino acid sequence which constitutes the TM region of proteins constituting any of S1PR2, S1PR4, and S1PR5 belonging to S1PR family, and has antitumor activity.

Regarding functions of the proteins, for example, the followings are known.

According to the above non-patent literature by Sukocheva and by Pyne et al., S1PR2 is a seven-transmembrane type membrane protein composed of typically about 353 amino acid residues and is a protein that binds to S1P and controls cancer cell motility.

According to the above non-patent literature by Sukocheva and by Pyne et al., S1PR4 is a seven-transmembrane type membrane protein composed of typically about 384 amino acid residues and is a protein that binds to S1P and controls proliferation of stem cells (oval cells) during liver damage due to the cells.

According to the above non-patent literature by Sukocheva and by Pyne et al., S1PR5 is a seven-transmembrane type membrane protein composed of typically about 398 amino acid residues and is a protein that binds to S1P and controls proliferation of cancer cells.

However, it has not been found that the TM region of S1PR described above has antitumor activity, and the fact that an artificially synthesized antitumor peptide is obtained by synthesizing an amino acid sequence of such a peptide region and adding a CPP to the sequence was not completely unexpected at the time of filing this application.

For example, as described in the above non-patent literature by Sukocheva and Pyne et al. genes encoding S1PR2, 4, and 5 (including the case of cDNA) have been found in mammals such as humans, mice, rats, and pigs. Here, S1PR gene information and amino acid sequence information can be obtained by accessing knowledge bases (databases) in various public international organizations. For example, all amino acid sequence information of S1PR derived from various species and TM region amino acid sequence information can be obtained in Universal Protein Resource (UniProt).

The S1PR-TM related sequences according to the above (1) preferably used for implementing the present invention are represented by SEQ ID NOs: 1 to 6.

Specifically, the amino acid sequence represented by SEQ ID NO: 1 is an amino acid sequence composed of a total of 29 amino acid residues constituting the 2nd TM region from the N-terminal of human-derived S1PR2.

In addition, the amino acid sequence represented by SEQ ID NO: 2 is an amino acid sequence composed of a total of 21 amino acid residues constituting the 2nd TM region from the N-terminal of human-derived S1PR4.

In addition, the amino acid sequence represented by SEQ ID NO: 3 is an amino acid sequence composed of a total of 21 amino acid residues constituting the 3rd TM region from the N-terminal of human-derived S1PR4.

In addition, the amino acid sequence represented by SEQ ID NO: 4 is an amino acid sequence composed of a total of 21 amino acid residues constituting the 4th TM region from the N-terminal of human-derived S1PR4.

In addition, the amino acid sequence represented by SEQ ID NO: 5 is an amino acid sequence composed of a total of 21 amino acid residues constituting the 3rd TM region from the N-terminal of human-derived S1PR5.

In addition, the amino acid sequence represented by SEQ ID NO: 6 is an amino acid sequence composed of a total of 21 amino acid residues constituting the 4th TM region from the N-terminal of human-derived S1PR5.

Here, in SEQ ID NOs: 1 to 6 as described above, TM sequences of human-derived S1PR2, 4, and 5 are shown, but the sequences are only examples, and available amino acid sequences are not limited thereto.

For example, SEQ ID NO: 7 represents an amino acid sequence composed of a total of 29 amino acid residues constituting the 2nd TM region from the N-terminal of mouse-derived S1PR2.

In addition, SEQ ID NO: 8 represents an amino acid sequence composed of a total of 29 amino acid residues constituting the 2nd TM region from the N-terminal of rat-derived S1PR2.

In addition, SEQ ID NO: 9 represents an amino acid sequence composed of a total of 21 amino acid residues constituting the 2nd TM region from the N-terminal of mouse- and rat-derived S1PR4.

In addition, SEQ ID NO: 10 represents an amino acid sequence composed of a total of 21 amino acid residues constituting the 3rd TM region from the N-terminal of mouse-, rat- and pig-derived S1PR4.

In addition, SEQ ID NO: 11 represents an amino acid sequence composed of a total of 21 amino acid residues constituting the 4th TM region from the N-terminal of mouse-derived S1PR4.

In addition, SEQ ID NO: 12 represents an amino acid sequence composed of a total of 23 amino acid residues constituting the 4th TM region from the N-terminal of rat-derived S1PR4.

In addition, SEQ ID NO: 13 represents an amino acid sequence composed of a total of 23 amino acid residues constituting the 4th TM region from the N-terminal of pig-derived S1PR4.

In addition, SEQ ID NO: 14 represents an amino acid sequence composed of a total of 21 amino acid residues constituting the 3rd TM region from the N-terminal of mouse-, rat- and pig-derived S1PR5.

In addition, SEQ ID NO: 15 represents an amino acid sequence composed of a total of 21 amino acid residues constituting the 4th TM region from the N-terminal of mouse-derived S1PR5.

In addition, SEQ ID NO: 16 represents an amino acid sequence composed of a total of 21 amino acid residues constituting the 4th TM region from the N-terminal of rat-derived S1PR5.

In addition, SEQ ID NO: 17 represents an amino acid sequence composed of a total of 21 amino acid residues constituting the 4th TM region from the N-terminal of pig-derived S1PR5.

Here, the amino acid sequence represented by SEQ ID NO: 2 is also an amino acid sequence constituting the 2nd TM region from the N-terminal of pig-derived S1PR4.

Regarding a CPP related sequence that is used to construct an antitumor peptide disclosed here, conventionally known various CPPs can be used. For example, a so-called polyarginine (Rn) composed of 3 or more, preferably 5 or more and 11 or less, and preferably 9 or less arginine residues, is suitable as a CPP used here. In addition, various known CPPs can be used.

Although not particularly limited, SEQ ID NOs: 18 to 35 represent preferable examples of a CPP. Specific descriptions are given below.

The amino acid sequence represented by SEQ ID NO: 18 corresponds to NoLS (Nucleolar localization signal) composed of a total of 14 amino acid residues derived from FGF2 (basic fibroblast growth factor).

The amino acid sequence represented by SEQ ID NO: 19 corresponds to NoLS composed of a total of 19 amino acid residues derived from one type (ApLLP) of nucleolar proteins.

The amino acid sequence represented by SEQ ID NO: 20 corresponds to NoLS composed of a total of 16 amino acid residues derived from a protein (γ(1)34.5) of HSV-1 (herpes simplex virus type 1).

The amino acid sequence represented by SEQ ID NO: 21 corresponds to NoLS composed of a total of 19 amino acid residues derived from a p40 protein of HIC (human I-mfa domain-containing protein).

The amino acid sequence represented by SEQ ID NO: 22 corresponds to NoLS composed of a total of 16 amino acid residues derived from an MEQ protein of MDV (Marek disease virus).

The amino acid sequence represented by SEQ ID NO: 23 corresponds to NoLS composed of a total of 17 amino acid residues derived from Survivin-deltaEx3 which is a protein that inhibits apoptosis.

The amino acid sequence represented by SEQ ID NO: 24 corresponds to NoLS composed of a total of 7 amino acid residues derived from Angiogenin which is a vascular growth factor.

The amino acid sequence represented by SEQ ID NO: 25 corresponds to NoLS composed of a total of 8 amino acid residues derived from MDM2 which is a nuclear phosphoprotein and forms a complex with a p53 tumor inhibiting protein.

The amino acid sequence represented by SEQ ID NO: 26 corresponds to NoLS composed of a total of 9 amino acid residues derived from GGNNVα which is a betanoda virus protein.

The amino acid sequence represented by SEQ ID NO: 27 corresponds to NoLS composed of a total of 7 amino acid residues derived from NF-κB-inducing kinase (NIK).

The amino acid sequence represented by SEQ ID NO: 28 corresponds to NoLS composed of a total of 15 amino acid residues derived from a Nuclear VCP-like protein.

The amino acid sequence represented by SEQ ID NO: 29 corresponds to NoLS composed of a total of 18 amino acid residues derived from p120 which is a nucleolar protein.

The amino acid sequence represented by SEQ ID NO: 30 corresponds to NoLS composed of a total of 14 amino acid residues derived from the ORF57 protein of HVS (herpesvirus saimiri).

The amino acid sequence represented by SEQ ID NO: 31 corresponds to NoLS composed of a total of 13 amino acid residues including amino acids 491-503 of LIM kinase 2 (LIM Kinase 2) present in human endothelial cells, which is one of protein kinase related to intracellular signal transduction.

The amino acid sequence represented by SEQ ID NO: 32 corresponds to NoLS composed of a total of 8 amino acid residues included in the N protein (nucleocapsid protein) of IBV (avian infectious bronchitis virus).

The amino acid sequence represented by SEQ ID NO: 33 corresponds to a membrane-permeable motif composed of a total of 9 amino acid sequences derived from the protein transduction domain included in TAT of HIV(Human Immunodeficiency Virus).

The amino acid sequence represented by SEQ ID NO: 34 corresponds to a membrane-permeable motif composed of a total of 11 amino acid sequences of the protein transduction domain (PTD4) obtained by modifying the above the TAT.

The amino acid sequence represented by SEQ ID NO: 35 corresponds to a membrane-permeable motif composed of a total of 18 amino acid sequences derived from ANT of Antennapedia which is a variant of *Drosophila*.

Among these, particularly, amino acid sequences related to NoLS and TAT (or modified amino acid sequences thereof) are preferable. For example, the CPP sequences related to NoLS as represented by SEQ ID NO: 31 and SEQ ID NO: 32 or the CPP sequences related to TAT and ANT as represented by SEQ ID NOs: 33 to 35 can be suitably used to construct the antitumor peptide disclosed here.

A peptide chain (amino acid sequence) of the antitumor peptide disclosed here may include:
(1) an S1PR-TM related sequence and
(2) a CPP related sequence as described above,
and either the S1PR-TM related sequence or the CPP related sequence may be relatively arranged on the N-terminal side (C-terminal side).

Preferably, the S1PR-TM related sequence and the CPP related sequence are arranged adjacent to each other. Specifically, there are preferably no amino acid residues that are not included in both sequence parts between the S1PR-TM related sequence and the CPP related sequence. Alternatively, even if there are amino acid residues, the number of amino acid residues functioning as a linker connecting the above two sequences is preferably 10 or less (more preferably 5 or less, for example, 1 to 2 amino acid residues).

As long as the antitumor activity with which proliferation of at least one type of tumor cells can be inhibited is not impaired, a sequence (amino acid residue) part other than the amino acid sequence constituting the S1PR-TM related sequence and the CPP related sequence can be contained.

In the antitumor peptide disclosed here, a total number of amino acid residues constituting the peptide chain is suitably 100 or less, preferably 80 or less, and preferably 70 or less (for example, a peptide chain of about 30 to 50). Such a peptide with a short chain length is easily chemically synthesized and an antitumor peptide can be easily provided. Although not particularly limited, a linear or helical form is preferable because it is less likely to become an immunogen (antigen). A peptide in such a form is less likely to constitute an epitope.

A proportion of the S1PR-TM related sequence and the CPP related sequence with respect to the total number of amino acid sequences of the synthesized peptide is not particularly limited as long as the antitumor activity is not impaired, but the proportion is desirably about 80% or more by number and preferably 90% or more by number. Here, it is preferable that all amino acid residues be L-type amino acids. However, some or all of amino acid residues may be substituted with D-type amino acids as long as the antitumor activity is not impaired.

Preferably, in the antitumor peptide disclosed here, at least one amino acid residue is preferably amidated. When a carboxyl group of an amino acid residue (typically, a C-terminal amino acid residue of the peptide chain) is amidated, it is possible to improve structural stability (for example, protease resistance) of the synthetic peptide. For example, when a CPP related sequence part constitutes a C-terminal of the antitumor peptide, the C-terminal amino acid residue of the sequence part is preferably amidated. On the other hand, when an S1PR-TM related sequence part constitutes a C-terminal of the antitumor peptide, the C-terminal amino acid residue of the sequence part is preferably amidated. In another preferable aspect, the stability of the synthetic peptide can be improved by amidating the C-terminal amino acid residue of the synthetic peptide having amino acid sequences represented by SEQ ID NOs: 36 to 41.

The antitumor peptide disclosed here can be easily produced according to a general chemical synthesis method. For example, any of conventionally known solid-phase synthesis methods and liquid phase synthesis methods may be used. A solid-phase synthesis method in which Boc (t-butyloxycarbonyl) or Fmoc (9-fluorenylmethoxycarbonyl) is applied as a protecting group for an amino group is suitable.

Regarding the antitumor peptide disclosed here, a peptide chain having a desired amino acid sequence and a modified (C-terminal amidation, etc.) part can be synthesized according to a solid-phase synthesis method using a commercially available peptide synthesizer.

Alternatively, an antitumor peptide may be biosynthesized based on a genetic engineering technique. That is, a polynucleotide (typically, DNA) of a nucleotide sequence (including an ATG start codon) that encodes an amino acid sequence of a desired antitumor peptide is synthesized. Then, a recombinant vector having a genetic construct for expression composed of the synthesized polynucleotide (DNA) and various regulatory elements (including promoters, ribosome binding sites, terminators, enhancers, and various cis elements that controls expression levels) for expressing the amino acid sequence in host cells is constructed according to host cells.

According to a general technique, the recombinant vector is introduced into predetermined host cells (for example yeast, insect cells, and plant cells), and the host cells or tissues or subjects containing the cells are cultured under predetermined conditions. Accordingly, desired peptides can be expressed and produced in cells. Then, peptides are isolated from the host cells (in a culture medium if secreted), and as necessary, refolding, purification, and the like are performed, and thereby a desired antitumor peptide can be obtained.

Here, regarding a method of constructing a recombinant vector, a method of introducing a constructed recombinant vector into host cells, and the like, methods conventionally used in the field may be directly used, and such methods themselves do not particularly characterize the present invention, and thus detailed description thereof will be omitted.

Alternatively, a template DNA (that is, a synthetic gene fragment including a nucleotide sequence that encodes an amino acid sequence of an antitumor peptide) for a cell-free protein synthesis system is constructed, various compounds (ATP, RNA polymerase, amino acids, etc.) necessary for peptide synthesis are used, and thus a desired polypeptide can be synthesized in vitro using a so-called cell-free protein synthesis system. Regarding the cell-free protein synthesis system, refer to, for example, the paper written by Shimizu et al. (Shimizu et al., Nature Biotechnology, 19, 751-755 (2001)), and the paper written by Madin et al. (Madin et al., Proc. Natl. Acad. Sci. USA, 97(2), 559-564 (2000)). Based on the techniques described in these papers, many companies had already commissioned polypeptides at the time of filing this application, and cell-free protein synthesis kits (for example, commercially available from CellFree Sciences Co., Ltd., Japan) are commercially available.

A single-stranded or double-stranded polynucleotide including a nucleotide sequence that encodes the antitumor peptide disclosed here and/or a nucleotide sequence complementary to the sequence can be easily produced (synthesized) by conventionally known methods. That is, when codons corresponding to amino acid residues constituting a designed amino acid sequence are selected, a nucleotide sequence corresponding to the amino acid sequence of the antitumor peptide is easily determined and provided. Then, the nucleotide sequence is determined once, a (single-stranded) polynucleotide corresponding to a desired nucleotide sequence can be easily obtained using a DNA synthesizer or the like. In addition, desired double-stranded DNA can be obtained using the obtained single-stranded DNA as a template according to various enzymatic synthesis techniques (typically, PCR). In addition, the polynucleotide may be in the form of DNA or in the form of RNA (mRNA, etc.). Double-stranded or single-stranded DNA may be provided. When single-stranded DNA is provided, it may be a coding strand (sense strand) or a non-coding strand (antisense strand) of a sequence complementary thereto.

The polynucleotide obtained in this manner can be used as a material for constructing a recombinant gene (expression cassette) for antitumor peptide production in various host cells or a cell-free protein synthesis system as described above.

The antitumor peptide disclosed here can be suitably used as an effective component of a composition for inhibiting (or suppressing) proliferation of tumor cells (that is, a pharmaceutical antitumor composition such as an antitumor agent). Here, the antitumor peptide may be in a salt form as long as the antitumor activity is not impaired. For example, an acid addition salt of the synthetic peptide that can be obtained by an addition reaction of an inorganic acid or organic acid that is generally used according to a general method can be used. Therefore, "peptide" described in this specification and the claims includes such salt forms.

The antitumor composition disclosed here can contain various pharmaceutically (pharmacologically) acceptable carriers according to the usage form as long as the antitumor activity of the antitumor peptide as an effective component is not impaired. For example, carriers that are generally used in the peptide drug can be applied as a diluent, an excipient, and the like.

The carrier may appropriately vary depending on applications and forms of the antitumor composition disclosed here, but typically, water, a physiological buffer solution, and various organic solvents may be exemplified. The carrier may be a non-drying oil such as an aqueous alcohol (such as ethanol) solution with an appropriate concentration, glycerol, and olive oil. Alternatively, it may be a liposome. In addition, examples of a secondary component that can be contained in the antitumor composition include various fillers, extending agents, binders, moisturizers, surfactants, pigments, and perfumes.

Examples of typical forms of the antitumor composition (antitumor agent) include solutions, suspending agents, emulsions, aerosols, foam agents, granules, powders, tablets, capsules, ointments, and aqueous gels. In addition, for use in injection or the like, lyophilizates and granules for preparing a drug solution by performing dissolving in a saline or a suitable buffer solution (for example, PBS) immediately before use can be provided.

Here, a process itself of preparing various forms of compositions (drugs) including the antitumor peptide (main component) and various carriers (minor component) as materials may be performed according to a conventional known method, and such a production method itself does not characterize the present invention, and thus detailed description thereof will be omitted. Examples of detailed sources of information on prescription include Comprehensive Medicinal Chemistry, edited by Corwin Hansch, Pergamon Press (1990). The entire content in this book is incorporated by reference.

Cells to which the antitumor composition disclosed here (antitumor peptide) are applied are not particularly limited as long as they are tumor cells (cancer cells), and the antitumor composition can be applied to various types of tumor cells that occur in humans or non-human mammals. For example, many types of squamous cell carcinoma and adenocarcinoma are included. For example, cancer cells of melanoma, lung cancer (non-small cell lung cancer, small cell lung cancer, alveolar basal epithelial adenocarcinoma, and the like), kidney cancer, and the like or cells of breast cancer, colon cancer, pancreatic cancer, skin cancer such as basal cell carcinoma, neuroblastoma, retinoblastoma, pheochromocytoma, and other cell tumors may be exemplified.

The antitumor composition disclosed here can be used according to a method and in a dose depending on its form and purpose as in a conventional peptide formulation. For example, only a desired amount of the antitumor composition in the form of a solution can be administered to affected parts (typically, malignant tumor tissues) of patients (that is, a living organism) through intravenous, intramuscular, subcutaneous, intradermal or intraperitoneal injection. Alternatively, a solid form such as a tablet or a gel-like or aqueous jelly-like form such as an ointment can be directly administered to predetermined tissues (that is, an affected part such as tissues and organs including tumor cells). Alternatively, a solid form such as a tablet can be administered orally. In the case of oral administration, in order to prevent digestive enzyme decomposition in the digestive tract, encapsulation or a protective (coating) material is preferably applied.

Alternatively, with respect to tumor cells (including culture cell lines and cell masses, tissues or organs extracted from living bodies) cultured outside a living organism (in vitro), an appropriate amount of the antitumor composition disclosed here (that is, an appropriate amount of the antitumor peptide) may be supplied to a culture medium containing target culture cells (tissues and the like) at least once. The amount supplied each time and the number of times it is supplied are not particularly limited because they can vary depending on conditions such as the type of tumor cells to be cultured, the cell density (cell density when the culture starts), passage number, culture conditions, and the type of the culture medium. However, the antitumor composition is preferably added once, twice, or more times so that a concentration of the antitumor peptide in the culture medium is within a range of about 5 µM or more and 100 µM or less, and preferably a range of 10 µM or more and 50 µM or less (for example, 12.5 µM or more and 25 µM or less).

The in vitro antitumor activity test method of the antitumor composition disclosed here is not particularly limited, but, a test using a cell proliferation measurement reagent using, for example, a tetrazolium salt, is preferably used. In a preferable embodiment, in an example in which the antitumor composition disclosed here is added, a cell proliferation rate (or cell viability) calculated in the test is lower than 30% (preferably 20%, and more preferably 10%) compared to a comparative example in which no antitumor composition disclosed here is added.

In addition, in still another embodiment, a specific cell viability to be described below (that is, an index of tumor cell selective antitumor activity) is lower than 50% (preferably 40% or 30%, more preferably 20%, and most preferably 10%).

While some examples of the present invention will be described below, the present invention is not intended to be limited to those shown in the examples.

Test Example 1: Synthesis of Peptide

A total of 6 peptides shown in Table 1 were produced using a commercially available peptide synthesizer. Details are as follows.

Sample 1 was designed as one example and was a synthetic peptide including the amino acid sequence represented by SEQ ID NO: 33 (TAT of HIV) as the CPP related sequence on the C-terminal side of the amino acid sequence (SEQ ID NO: 1) of the 2nd TM region from the N-terminal of human S1PR2 (SEQ ID NO: 36).

Sample 2 was designed as one example and was a synthetic peptide including the amino acid sequence represented by SEQ ID NO: 33 (TAT of HIV) as the CPP related sequence on the C-terminal side of the amino acid sequence (SEQ ID NO: 2) of the 2nd TM region from the N-terminal of human S1PR4 (SEQ ID NO: 37).

Sample 3 was designed as one example and was a synthetic peptide including the amino acid sequence represented by SEQ ID NO: 33 (TAT of HIV) as the CPP related sequence on the C-terminal side of the amino acid sequence (SEQ ID NO: 3) of the 3rd TM region from the N-terminal of human S1PR4 (SEQ ID NO: 38).

Sample 4 was designed as one example and was a synthetic peptide including the amino acid sequence represented by SEQ ID NO: 33 (TAT of HIV) as the CPP related sequence on the C-terminal side of the amino acid sequence (SEQ ID NO: 4) of the 4th TM region from the N-terminal of human S1PR4 (SEQ ID NO: 39).

Sample 5 was designed as one example and was a synthetic peptide including the amino acid sequence represented by SEQ ID NO: 33 (TAT of HIV) as the CPP related sequence on the C-terminal side of the amino acid sequence (SEQ ID NO: 5) of the 3rd TM region from the N-terminal of human S1PR5 (SEQ ID NO: 40).

Sample 6 was designed as one example and was a synthetic peptide including the amino acid sequence represented by SEQ ID NO: 33 (TAT of HIV) as the CPP related sequence on the C-terminal side of the amino acid sequence (SEQ ID NO: 6) of the 4th TM region from the N-terminal of human S1PR5 (SEQ ID NO: 41).

TABLE 1

| | Amino acid sequences of synthetic peptides subjected to the test | | |
|---|---|---|---|
| Sample No. | Amino acid sequence | Total number of amino acid residues | SEQ ID NO: |
| 1 | AMYLFLGNLAASDLLAGVAFVA NTLLSGSRKKRRQRRR-CONH$_2$ | 38 | 36 |

TABLE 1-continued

Amino acid sequences of synthetic peptides subjected to the test

| Sample No. | Amino acid sequence | Total number of amino acid residues | SEQ ID NO: |
|---|---|---|---|
| 2 | LVNITLSDLLTGAAYLANVLLR KKRRQRRR-CONH$_2$ | 30 | 37 |
| 3 | WFLREGLLFTALAASTFSLLFR KKRRQRRR-CONH$_2$ | 30 | 38 |
| 4 | VYGFIGLCWLLAALLGMLPLLR KKRRQRRR-CONH$_2$ | 30 | 39 |
| 5 | EGGVFVALTASVLSLLAIALER KKRRQRRR-CONH$_2$ | 30 | 40 |
| 6 | LAMAAAAWGVSLLLGLLPALGR KKRRQRRR-CONH$_2$ | 30 | 41 |

All of the peptides of Samples 1 to 6 were synthesized by performing a solid-phase synthesis method (Fmoc method) manually using a commercially available peptide synthesizer. Here, since a manner of use of the peptide synthesizer itself does not characterize the present invention, detailed description thereof will be omitted. Here, in all synthetic peptides shown in Table 1, in the peptide having an amino acid sequence represented by a corresponding SEQ ID NO, a carboxyl group (—COOH) of the C-terminal amino acid was amidated (—CONH$_2$).

The synthesized peptides of the samples were dissolved in DMSO (dimethyl sulfoxide), and stock solutions (with a concentration of 2.5 mM) containing the sample peptides were prepared.

Test Example 2: Evaluation Test (1) of Antitumor Activity of Synthetic Peptides

The antitumor activity of the sample peptides synthesized in Test Example 1 was evaluated using human-derived cultured tumor cells as targets.

Specifically, currently commercially available human melanoma (A2058) cell lines were used as test tumor cells. In addition, a normal human mammary epithelial cell culture line (MCF-12F) was used for comparison. Here, culture solutions of respective cells are as follows.
(1) A2058 Cells:
DMEM culture medium including 2 mM L-glutamine, 0.1 mM of non-essential amino acids, 50 units/mL of penicillin, 50 μg/mL of streptomycin, and 10% fetal bovine serum (FBS) (product, commercially available from Wako Pure Chemical Industries, Ltd.). (2) MCF-12F cells:
DMEM/F12 culture medium including 20 ng/mL of recombinant EGF, 10 μg/mL of insulin, 0.5 μg/mL of hydrocortisone, and 10% FBS (product, commercially available from Wako Pure Chemical Industries, Ltd.).

Details of the test are as follows.

A2058 cells and MCF-12F cells were cultured and prepared so that the number of cells per well in a 96-well plate was about 5×10$^3$. An amount of the culture medium in this case was 100 μL per well.

Next, the 96-well plate was placed in a CO$_2$ incubator and pre-incubated under conditions of 37° C. and 5% CO$_2$ for about 1 day (21 hours to 24 hours).

Then, peptide-containing test culture mediums for each concentration were prepared so that the concentrations of the sample peptides to be evaluated were 12.5 μM and 25 μM, and supplied to wells (that is, wells after the pre-incubation) in which 90 μL of cells to be evaluated were cultured in each well. Then, the 96-well plate was returned to the CO$_2$ incubator and incubated under conditions of 37° C. and 5% CO$_2$ for 48 hours.

Here, the number of test wells (n) at peptide concentrations in peptide addition test groups was set to 3. Therefore, the value of the result shown in the following table is an average value of the results obtained in three test wells. First, the cell viability (%) was determined as follows.

After the incubation for 48 hours was completed, the culture medium in each well was replaced with 100 μL of a fresh culture medium containing no peptide, and additionally, 10 μL of a cell proliferation measurement reagent "Cell Counting Kit-8" (product, commercially available from Dojindo Molecular Technologies, Inc.) containing a "water-soluble tetrazolium salt (WST-8)" as a coloring reagent was added to each well. Then, the 96-well plate was returned to the CO$_2$ incubator and incubated under conditions of 37° C., and 5% CO$_2$ for 1.5 hours to 2 hours.

After the incubation was completed, the cell culture solution to which the reagent was added was collected and the cell viability (%) was evaluated according to a colorimetric method in which an absorbance at a wavelength of 450 nm (value corrected by the absorbance at a wavelength of 650 nm: A450-A650) was measured based on the reduction of the tetrazolium salt. Specifically, a measured value (measured absorbance) of a comparative test group in which the above incubation was performed for 48 hours simply in a culture medium containing no peptide was set as a cell viability of 100%, and the cell viability (%) was calculated from the measured absorbance of each test cell line as a relative value.

As a result, the A2058 cell viabilities of test groups in which any of the sample peptides used here (Samples 1 to 6) was contained in the culture medium so that the concentration thereof was 25 μM were all less than 10%. Specifically, the survival rate was 0.7% in the test group of Sample 1, 0.1% in the test group of Sample 2, 4.6% in the test group of Sample 3, 5.3% in the test group of Sample 4, 5.5% in the test group of Sample 5, and 0.5% in the test group of Sample 6. These results indicate that the sample peptides had strong antitumor activity.

Next, when the sample peptides were added to culture mediums, the survival rate of normal cells and the survival rate of test tumor cells were compared, and the tumor cell selective antitumor activity was evaluated.

Specifically, a value (value multiplied by 100 for convenience) obtained by dividing the cell viability of target tumor cells (here, A2058 cells) when the sample peptides were added at a concentration of 12.5 μM or 25 μM measured as described above by the cell viability of comparative normal cells (here, MCF-12F cells) measured under the same conditions, that is, $$\{(A2058\ cell\ viability)/(MCF\text{-}12F\ cell\ viability)\} \times 100$$

was calculated as a specific cell viability of the tumor cells, and the test tumor cells selective antitumor activity with respect to normal cells was evaluated using such a specific cell viability as an index. The results are shown in Table 2.

As can be clearly understood from the results shown in Table 2, the synthetic peptides of Samples 1 to 6 exhibited selective antitumor activity with respect to A2058 cells except a test group under 12.5 μM concentration conditions of Sample 1. It is known that A2058 cells are highly malignant in human melanoma cell lines and are resistant to many antitumor compositions. The above test results indicate that the sample peptides had strong antitumor activity and selective antitumor activity with respect to such A2058 cells.

TABLE 2

Specific cell viability when sample peptides were used

| Sample peptide No. | Peptide concentration (μM) | |
|---|---|---|
| | 12.5 | 25 |
| Sample 1 | 114.85 | 16.67 |
| Sample 2 | 4.79 | 1.96 |
| Sample 3 | 68.20 | 25.41 |
| Sample 4 | 46.80 | 35.10 |
| Sample 5 | 88.08 | 10.09 |
| Sample 6 | 40 | 5.88 |

(test tumor cell line: A2058)

Test Example 3: Evaluation Test (2) of Antitumor Activity of Synthetic Peptides

The antitumor activity and antitumor cell selective antitumor activity of Samples 2 and 6 of Test Example 1, with respect to a plurality of types of human-derived cultured tumor cells were evaluated.

Specifically, currently commercially available human melanoma cell lines (SK-MEL5), human non-small cell lung cancer cell lines (H2444), and human colorectal cancer cell lines (SW480) were used as test tumor cells. In addition, the above MCF-12F cells were used as normal cells for comparison.

For culture of cell lines, the following culture mediums were used.
(1) Human Melanoma Cell Lines (SK-MEL5):
E-MEM culture medium including 1 mM of sodium pyruvate, 100 unit/mL of penicillin, 100 μg/mL of streptomycin, and 10% FBS (product, commercially available from Wako Pure Chemical Industries, Ltd.)
(2) Human Lung Cancer Cell Lines (H2444):
RPMI-1640 culture medium including 2 mM of L-glutamine, 1 mM of sodium pyruvate, 10 mM of HEPES, 4,500 mg/mL of glucose, 50 units/mL of penicillin, 50 μg/mL of streptomycin, and 10% FBS (product, commercially available from Wako Pure Chemical Industries, Ltd.)
(3) Human Colorectal Cancer Cell Line (SW480):
Leibovitz's L-15 culture medium including 100 unit/mL of penicillin, 100 μg/mL of streptomycin, and 10% FBS (product, commercially available from Gibco)
Here, in the evaluation test using SW480 cell lines, the cells were cultured under conditions of 37° C. and without $CO_2$.

Then, the cell viability was calculated in the same processes as in Test Example 2. Here, in this test example, the antitumor activity of Sample 6 with respect to SK-MEL5 cells, the antitumor activity of Sample 2 with respect to H2444 cells, and the antitumor activity of Sample 2 and Sample 6 with respect to SW480 cells were evaluated.

As a result, the cell viability of tumor cells of the test groups in which Sample 2 or Sample 6 was contained in the culture medium so that the concentration thereof was 25 μM was about 20% or less, or even equal to or less than that (less than 10%). Specifically, the cell viability of SK-MEL5 cells subjected to Sample 6 was 1.9%, the cell viability of H2444 cells subjected to Sample 2 was 2.1%, the cell viability of SW480 cells subjected to Sample 2 was 2.3%, and the cell viability of SW480 cells subjected to Sample 6 was 20.2%.

Next, a specific cell viability was calculated in the same processes as in Test Example 2. That is, {(Test tumor cell survival rate)/(MCF-12F cell viability)}×100 was calculated as a specific cell viability of the tumor cells, and a test tumor cells selective antitumor activity with respect to normal cells was evaluated using such a specific cell viability as an index. The results are shown in Table 3 and Table 4. As can be clearly understood from the results, it was confirmed that both the synthetic peptides of Sample 2 and Sample 6 had strong antitumor activity and selective antitumor activity with respect to tumor cells subjected to this test example. This indicates that the antitumor peptide disclosed here can be applied to not only one type of tumor cell but also different types of tumor cells.

TABLE 3

Specific cell viability when Sample 2 was used

| Test tumor cell line | Peptide concentration of Sample 2 (μM) | |
|---|---|---|
| | 12.5 | 25 |
| H2444 | 0.22 | 0.41 |
| SW480 | 2.98 | 0.45 |

TABLE 4

Specific cell viability when Sample 6 was used

| Test tumor cell line | Peptide concentration of Sample 6 (μM) | |
|---|---|---|
| | 12.5 | 25 |
| SK-MEL5 | 0.25 | 0.22 |
| SW480 | 1.14 | 2.38 |

As described above, according to the antitumor peptide disclosed here, it is possible to suppress (or inhibit) proliferation of tumor cells. Therefore, it is possible to provide an antitumor composition (antitumor agent) that inhibits proliferation of at least one type of tumor cells using the antitumor peptide provided according to the present invention.

The invention claimed is:

1. A synthetic peptide inhibiting proliferation of at least one type of tumor cell, comprising the amino acid sequence selected from the group consisting of SEQ ID NOs: 36 to 41, wherein the total number of amino acid residues is 100 or less.

2. An antitumor composition inhibiting proliferation of at least one type of tumor cell, comprising:

a synthetic peptide; and at least one pharmaceutically acceptable carrier, wherein the synthetic peptide comprises the amino acid sequence selected from the group consisting of SEQ ID NOs: 36 to 41, and the total number of amino acid residues is 100 or less.

* * * * *